US 6,656,112 B2

(12) United States Patent
Miyanaga

(10) Patent No.: US 6,656,112 B2
(45) Date of Patent: Dec. 2, 2003

(54) DISTAL ENDOSCOPE PART HAVING LIGHT EMITTING SOURCE SUCH AS LIGHT EMITTING DIODES AS ILLUMINATING MEANS

(75) Inventor: Hirofumi Miyanaga, Hachioji (JP)

(73) Assignee: Olympus Optical Co., Ltd. (JP)

( * ) Notice: Subject to any disclaimer, the term of this patent is extended or adjusted under 35 U.S.C. 154(b) by 0 days.

(21) Appl. No.: 10/213,748

(22) Filed: Aug. 5, 2002

(65) Prior Publication Data

US 2002/0188177 A1 Dec. 12, 2002

Related U.S. Application Data

(62) Division of application No. 09/391,279, filed on Sep. 7, 1999, now Pat. No. 6,488,619.

(30) Foreign Application Priority Data

Sep. 8, 1998 (JP) ............................................ 10-254260
Sep. 8, 1998 (JP) ............................................ 10-254261

(51) Int. Cl.[7] .................................................. A61B 1/06
(52) U.S. Cl. ....................... 600/179; 600/170; 600/129; 600/130
(58) Field of Search ................................ 600/179, 178, 600/176, 177, 170, 160, 109, 129, 130; 348/65; 362/311

(56) References Cited

U.S. PATENT DOCUMENTS

| 4,652,093 | A | * | 3/1987 | Stephen et al. ................ 356/23 |
| 4,843,280 | A | * | 6/1989 | Lumbard et al. ............ 313/500 |
| 5,908,294 | A | * | 6/1999 | Schick et al. .................. 433/29 |
| 6,190,309 | B1 | * | 2/2001 | Ooshima et al. ............ 600/179 |
| 6,204,523 | B1 | * | 3/2001 | Carey et al. ................... 257/98 |
| 6,217,512 | B1 | * | 4/2001 | Salo et al. ................... 600/160 |

FOREIGN PATENT DOCUMENTS

| DE | 29612103 | * | 11/1997 |
| JP | 63-260526 | * | 10/1988 |
| JP | 8-117184 | * | 5/1996 |

* cited by examiner

Primary Examiner—John P. Leubecker
(74) Attorney, Agent, or Firm—Ostrolenk, Faber, Gerb & Soffen, LLP

(57) ABSTRACT

A substrate having a plurality of light emitting diodes united therewith lies on a plane containing the longitudinal axis of an insertion unit of an endoscope and its neighborhood. Likewise, part of a first objective surface lies on the plane containing the longitudinal axis of the insertion unit of the endoscope and its neighborhood. As long as the diameter of the insertion unit remains unchanged, the plane containing the longitudinal axis of the insertion unit of the endoscope and its neighborhood provides the largest area for the light emitting diodes. The light emitting diode sub-assembly is therefore placed on the plane, whereby the outer diameter of a distal endoscope part can be made as small as possible.

9 Claims, 15 Drawing Sheets

DISTAL ENDOSCOPE PART HAVING LIGHT EMITTING SOURCE SUCH AS LIGHT EMITTING DIODES AS ILLUMINATING MEANS

CROSS REFERENCE TO RELATED APPLICATION

This is a divisional of U.S. patent application Ser. No. 09/391,279, filed Sep. 7, 1999, now U.S. Pat. No. 6,488,619 in the name of Hirofumi MIYANAGA and entitled "DISTAL ENDOSCOPE PART HAVING LIGHT EMITTING SOURCE SUCH AS LIGHT EMITTING DIODES AS ILLUMINATING MEANS".

BACKGROUND OF THE INVENTION

1. Field of the Invention

The present invention relates to a distal endoscope part, or more particularly, a distal endoscope part characterized by a portion thereof in which light emitting diodes serving as an illuminating means are placed.

2. Description of the Related Art

Structures having a light emitting source such as light emitting diodes incorporated as an illuminating means in a distal endoscope part have been proposed in the past.

For example, Japanese Unexamined Patent Publication No. 63-260526 describes a distal endoscope part for side viewing in which a plurality of light emitting diodes is placed circumferentially with an objective optical system as a center in order to improve the light emitting characteristic of the distal part.

However, according to the related art (Japanese Unexamined Patent Publication No. 63-260526), the light emitting diodes are placed on a spherical surface on the outer circumference of an endoscope. The plurality of light emitting diodes must be attached one by one to a distal member.

When the light emitting diodes must be attached one by one to the distal endoscope member, there is difficulty in narrowing the spacing between adjoining light emitting diodes. A side viewing endoscope having a plurality of light emitting diodes placed on the outer circumference of an objective optical system has a drawback that the distal part thereof is large in size.

Moreover, Japanese Unexamined Patent Publication No. 8-117184 has proposed a structure having a light emitting source as an illuminating means incorporated in a distal endoscope part. Japanese Utility Model Registration No. 3007137 has proposed a structure having light emitting diodes as an illuminating means placed around a camera in a distal part of a tubular examination camera system. In these structures, the light emitting unit is protected with a cover glass or acrylic plate placed on the front surface thereof.

Especially in the Japanese Utility Model Registration No. 3007137, the cover glass over the front surfaces of the light emitting diodes also works to leave the light emitting diodes watertight.

However, when a watertight structure is realized using a transparent member such as the cover glass as it is as described in the related art, the cover glass must have a thickness large enough to position the perimeter thereof relative to a metallic member and support it. In the structure having the cover glass, therefore, mechanical members must be made larger by a dimension corresponding to the perimeter used for positioning.

As described in the Japanese Utility Model Registration No. 3007137, a structure has the light emitting diodes, which serves as an illuminating means, placed on the outer circumference of an imaging unit and a transparent member placed on the front surfaces of the light emitting diodes. This poses a problem in that the outer diameter of the distal part must be made larger by a dimension corresponding to the perimeter of the transparent member.

SUMMARY OF THE INVENTION

An object of the present invention is to provide a distal endoscope part making it possible to realize a side viewing endoscope having a plurality of light emitting diodes placed on the outer circumference of an objective optical system without an increase in the outer diameter of the distal part.

Another object of the present invention is to provide a distal endoscope part making it possible to realize a watertight structure without the necessities of placing a transparent member over the front surfaces of light emitting diodes and of increasing the outer diameter of the distal part.

A distal endoscope part in accordance with the present invention has a plurality of light emitting diodes for supplying illumination light placed as an illuminating means on the outer circumference of an objective optical system. The plurality of light emitting diodes is mounted on a substrate and united therewith. A sub-assembly of the plurality of united light emitting diodes is placed on a plane containing the longitudinal axis of an insertion unit of an endoscope and its neighborhood. Consequently, although the side viewing endoscope has the plurality of light emitting diodes placed on the outer circumference of the objective optical system, the outer diameter of the distal part thereof is not large in size.

Other features of the present invention and advantages thereof will be fully apparent from the description below.

BRIEF DESCRIPTION OF THE DRAWINGS

FIG. 1 shows the configuration of a side viewing endoscope;

FIG. 2 is a longitudinal sectional view showing the structure of a distal endoscope part shown in FIG. 1;

FIG. 3 is a cross sectional view of the A—A plane of the distal endoscope part shown in FIG. 2;

FIG. 4 is a top view of the distal endoscope part shown in FIG. 2;

FIG. 5 is a longitudinal sectional view showing the BB plane of the distal endoscope part shown in FIG. 4;

FIG. 6 is a cross sectional view showing the C—C plane of the distal endoscope part shown in FIG. 2;

FIG. 7 is a first explanatory diagram for explaining a first variant of the distal endoscope part shown in FIG. 1;

FIG. 8 is a second explanatory diagram for explaining the first variant of the distal endoscope part shown in FIG. 1;

FIG. 9 is a first explanatory diagram for explaining a second variant of the distal endoscope part shown in FIG. 1;

FIG. 10 is a second explanatory diagram for explaining a second variant of the distal endoscope part shown in FIG. 1;

FIG. 11 shows the configuration of a side viewing endoscope;

FIG. 12 is a longitudinal sectional view showing the structure of the distal endoscope part shown in FIG. 11;

FIG. 13 is a cross sectional view showing the A—A plane of the distal endoscope part shown in FIG. 12;

FIG. 14 is a top view of the distal endoscope part shown in FIG. 12;

FIG. 15 is a longitudinal sectional view showing the B—B plane of the distal endoscope part shown in FIG. 12;

FIG. 16 is a cross sectional view showing the C—C plane of the distal endoscope part shown in FIG. 12;

FIG. 17 is a cross sectional view showing the D—D plane of the distal endoscope part shown in FIG. 12;

FIG. 18 is a cross sectional view showing the E—E plane of the distal endoscope part shown in FIG. 12;

FIG. 19 is a longitudinal sectional view showing the structure of a control unit included in the distal endoscope part shown in FIG. 11;

FIG. 20 shows the structure of a variant of the control unit shown in FIG. 19;

FIG. 21 shows the structure of a light emitting diode included in the distal endoscope part shown in FIG. 14;

FIG. 22 is a longitudinal sectional view showing the structure of a distal endoscope part;

FIG. 23 is a cross sectional view showing the F—F plane of the distal endoscope part shown in FIG. 22; and FIG. 24 is a cross sectional view showing the G—G plane of the distal endoscope part shown in FIG. 22.

DESCRIPTION OF THE PREFERRED EMBODIMENTS

First Embodiment

Figure 1:
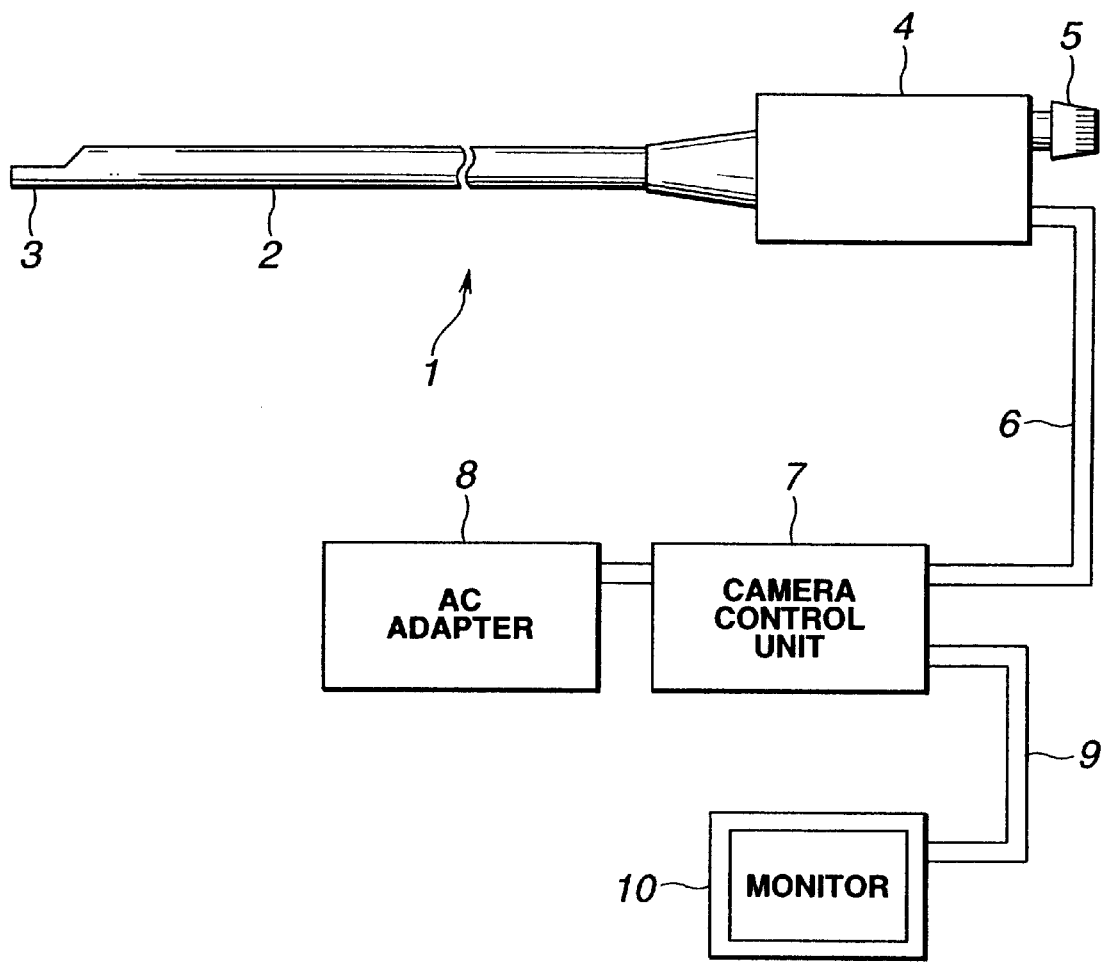
FIG. 1 to FIG. 10 relate to the first embodiment of the present invention.

As shown in FIG. 1, a side viewing endoscope 1 has an insertion unit 2 to be inserted into an intracorporeal cavity. A distal endoscope part (hereinafter referred to as a distal part) in accordance with the present invention attached to the distal end of the insertion unit 2 includes an imaging means and light emitting diodes serving as an illuminating means. A control unit attached to the proximal end of the insertion unit 2 has a light level adjustment knob 5 used to adjust an amount of light emitted from the light emitting diodes in the distal part 3.

An optical image of an object illuminated the light emitting diodes is projected on an imaging unit included in the distal part 3, and converted into an electric signal. The electric signal is sent to a camera control unit 7 over a camera control cable 6. Image data represented by the electric signal is processed by the camera control unit 7 that is powered by an AC adapter 8. An image signal produced by the camera control unit 7 is transferred to a monitor 10 over a monitor cable 9. An endoscopic image is then displayed.

Figure 2:
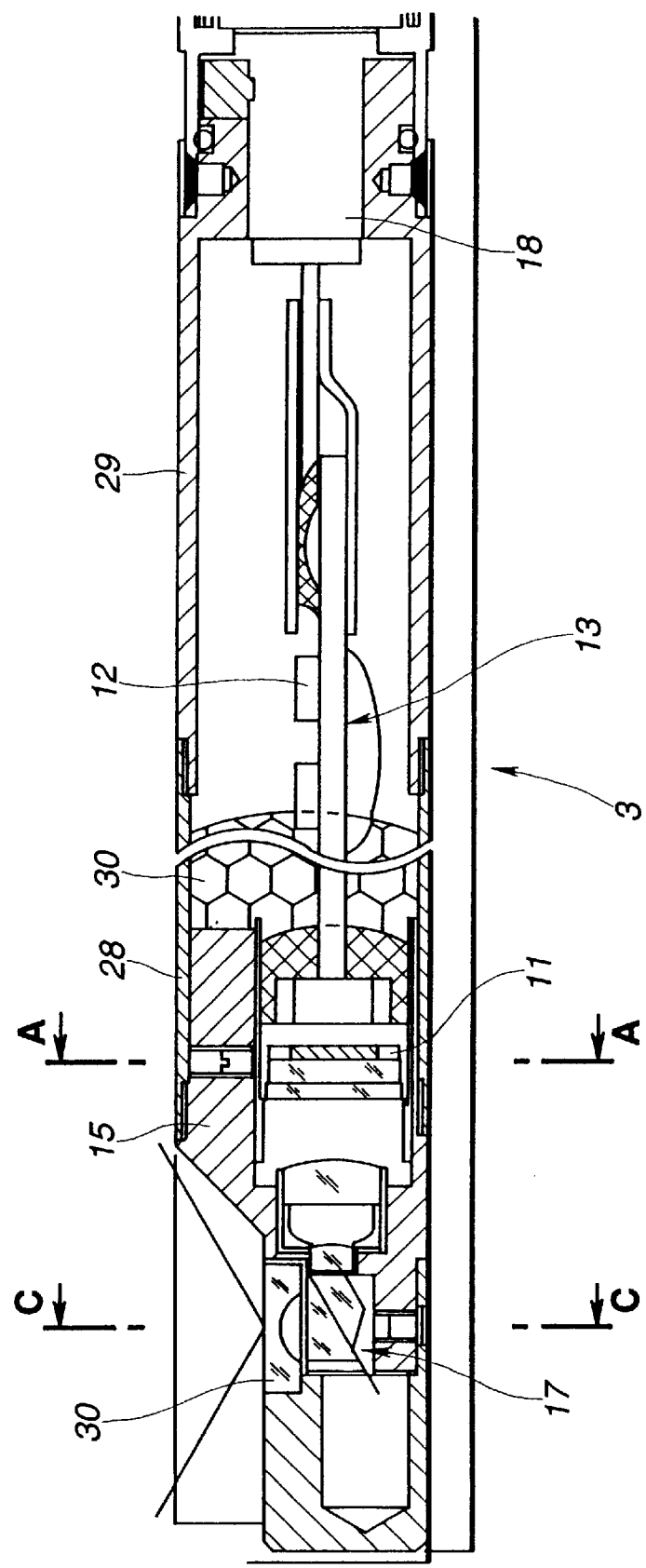
Figure 3:
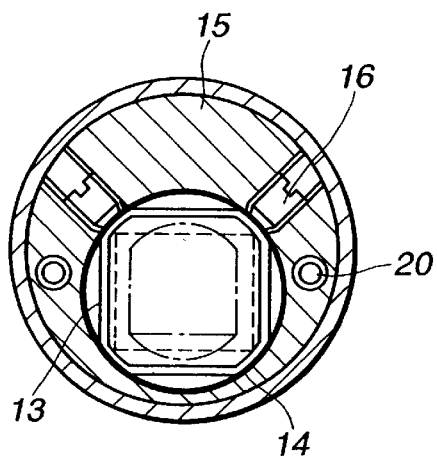

As shown in FIG. 2 and FIG. 3, an imaging unit 13 for converting an optical signal into an electric signal is fixed to a body 15 with a holder 14 between them by means of screws 16. The imaging unit 13 consists of a solid-state imaging device 11 and electronic parts 12.

An objective sub-assembly 17 for converging an optical image at the solid-state imaging device 11 is placed ahead of the solid-state imaging device 11. The optical image represents an object located in a direction of side viewing (at a right angle with respect to the longitudinal direction of the insertion unit 2).

A signal cable 18 over which a signal is transferred from the camera control unit 7 to the imaging unit 13, and power cables 20 over which power is supplied to the light emitting diodes 19 serving as an illuminating means are passed through the insertion unit 2.

Figure 4:
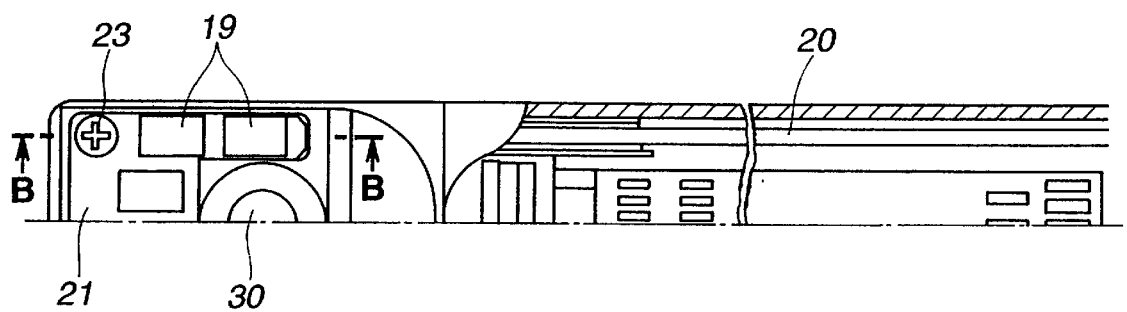
Figure 5:
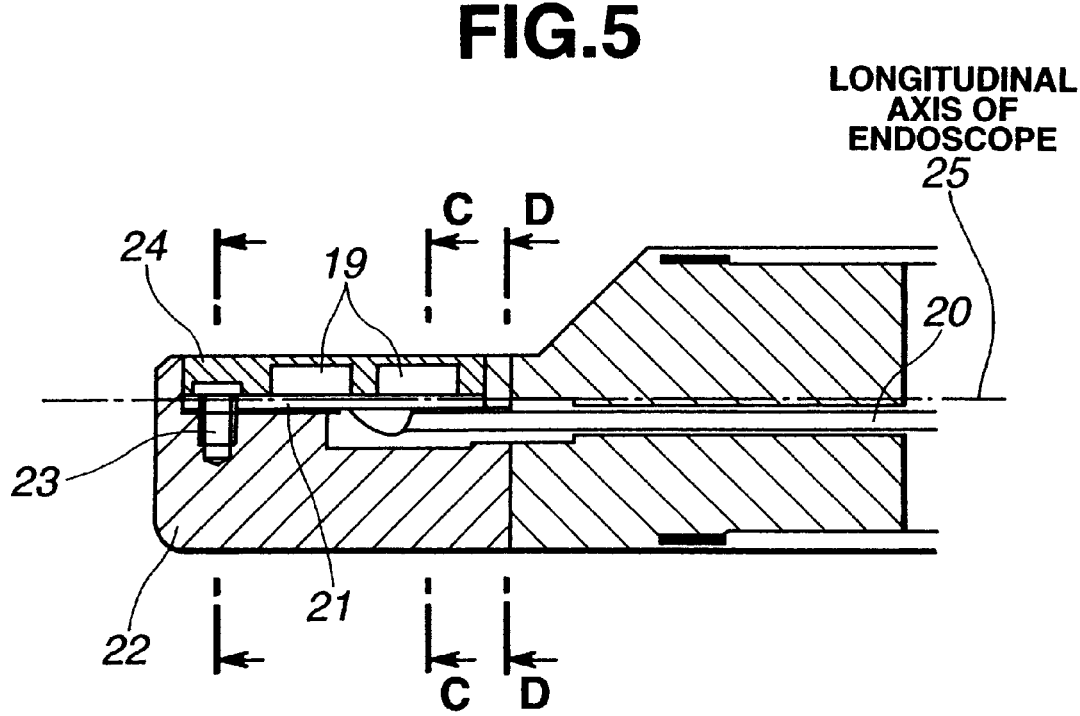
Figure 6:
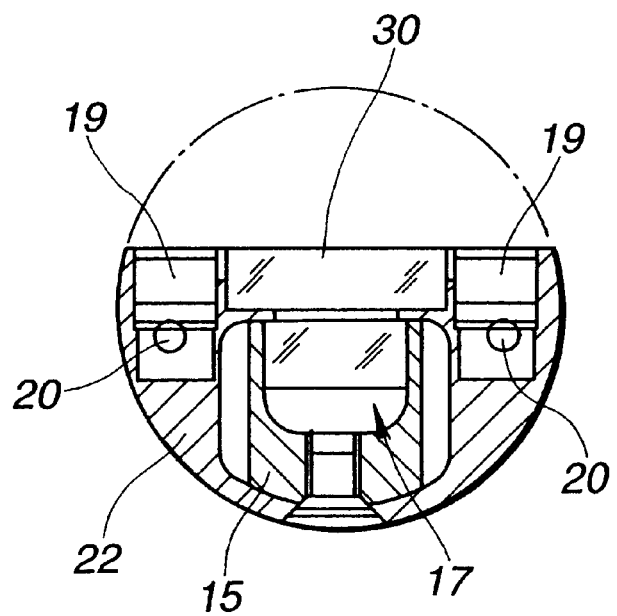

As shown in FIG. 4 to FIG. 6, the light emitting diodes 19 serving as an illuminating means for irradiating illumination light in the direction of side viewing (at a right angle with respect to the longitudinal direction of the insertion unit 2) are soldered to a substrate 21. The power cables 20 are also soldered to the substrate 21. The substrate 21 having the light emitting diodes and power cables united therewith is fixed to a body 22 by means of screws A 23.

The substrate 21 having the plurality of light emitting diodes 19 united therewith lies on a plane containing the longitudinal axis 25 of the insertion unit and its neighborhood.

Likewise, part of a first objective surface 30 lies on the plane containing the longitudinal axis 25 of the insertion unit of the endoscope and its neighborhood. As long as the outer diameter of the endoscope remains unchanged, the plane containing the longitudinal axis 25 of the insertion unit and its neighborhood provides the largest area for the light emitting diodes. If the light emitting diode sub-assembly 19 is placed on the plane, the outer diameter of the distal part 3 can be made as small as possible.

The light emitting diodes 19 are fixed to the body 22 together with the substrate 21. Thereafter, a substantially transparent filler 24 is injected to fully cover the surroundings of the light emitting diodes 19 and the light emitting surfaces thereof. Even the tops of the light emitting diodes 19 are covered with the filler 24, whereby the light emitting diodes 19 are not only protected to be blocked from outside but also left watertight.

Figure 7:
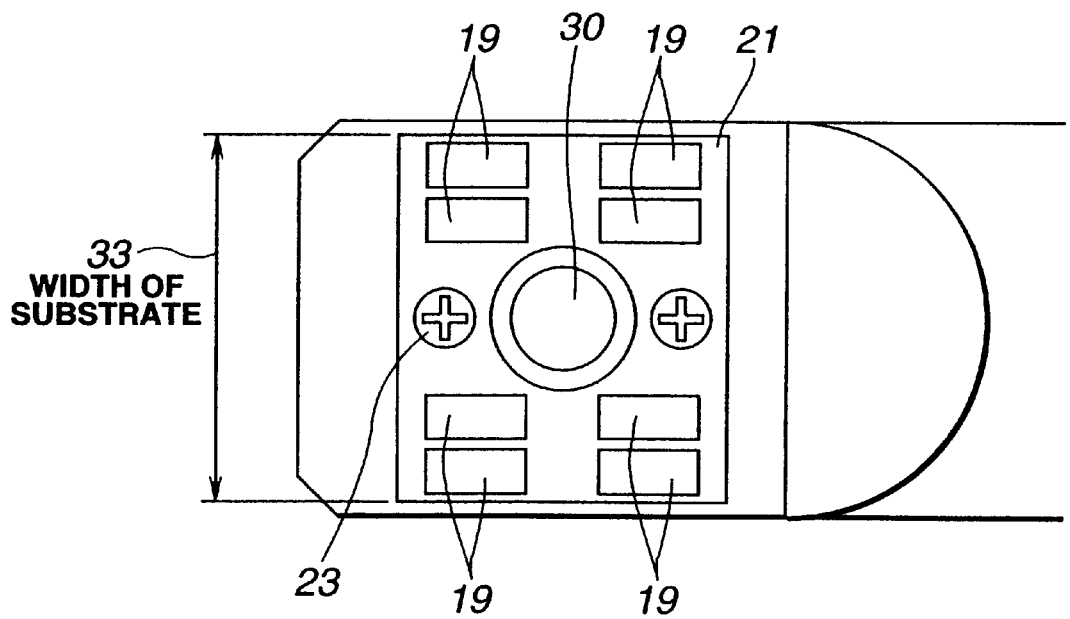
Figure 8:
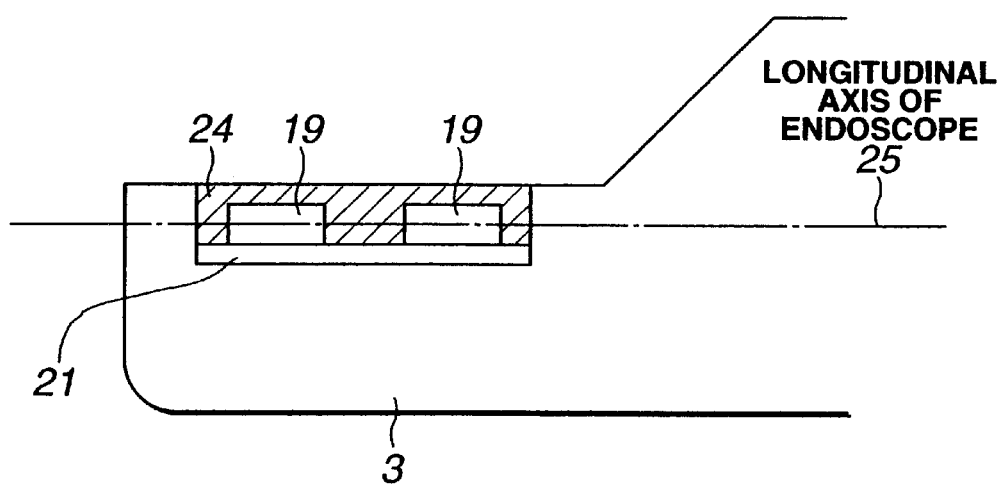

The light emitting diodes 19 on the substrate 21 may be, as shown in FIG. 7 and FIG. 8, mounted in pairs. In this case, the sub-assembly of the light emitting diodes mounted on the substrate 21 is attached to a distal mechanical member 32. Paired light emitting diodes 19 can therefore be located mutually as closely as possible. Consequently, the width 33 of the substrate can be decreased and the outer diameter of the distal part can be minimized.

Figure 9:
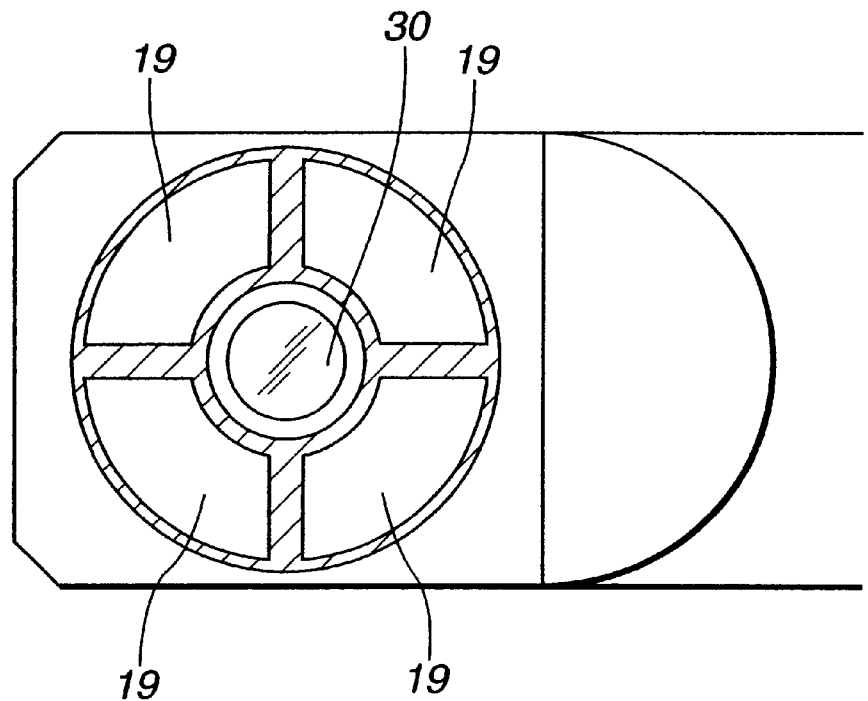
Figure 10:
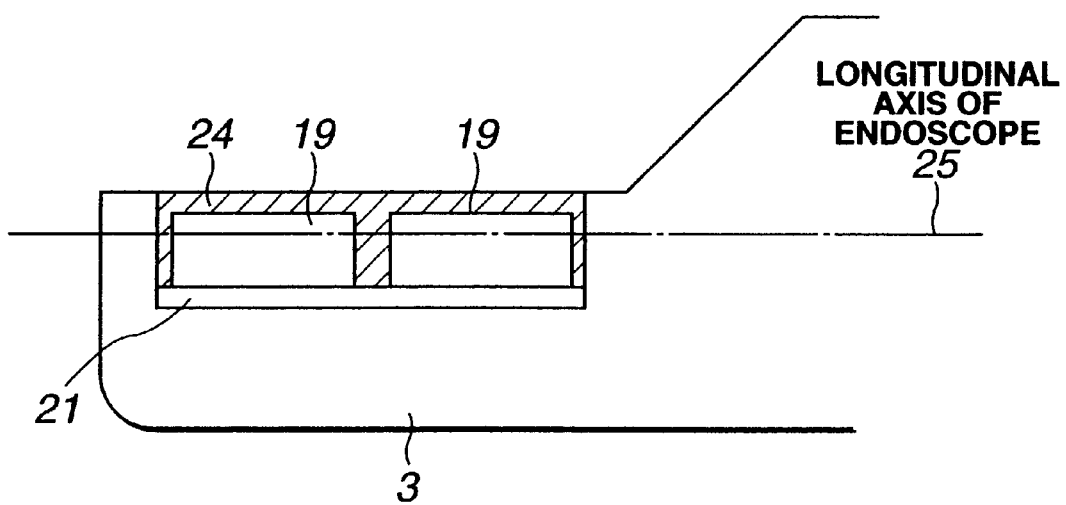

Moreover, as shown in FIG. 9 and FIG. 10, a package for each light emitting diode 19 may be shaped like a sector in order to improve the density of mounted components and the efficiency in emitting light.

As mentioned above, according to the present embodiment, the substrate 21 having the plurality of light emitting diodes 19 united therewith is placed on the plane containing the longitudinal axis 25 of the insertion unit and its neighborhood. Part of the first objective surface 30 is also placed on the plane containing the longitudinal axis 25 of the insertion unit and its neighborhood. As long as the outer diameter of the endoscope remains unchanged, the plane containing the longitudinal axis 25 of the insertion unit and its neighborhood can provide the largest area for the light emitting diodes. For this reason, the outer diameter of the distal part 3 can be minimized.

In other words, the light emitting diode sub-assembly made by mounting the plurality of light emitting diodes on the substrate is placed on the plane containing the longitudinal axis 25 of the insertion unit and its neighborhood. Therefore, the density of mounted components can be improved and the outer diameter of the distal endoscope part can be minimized.

Moreover, the plurality of light emitting diodes can be assembled at a time. This leads to easy assembling.

Second Embodiment

Figure 11:
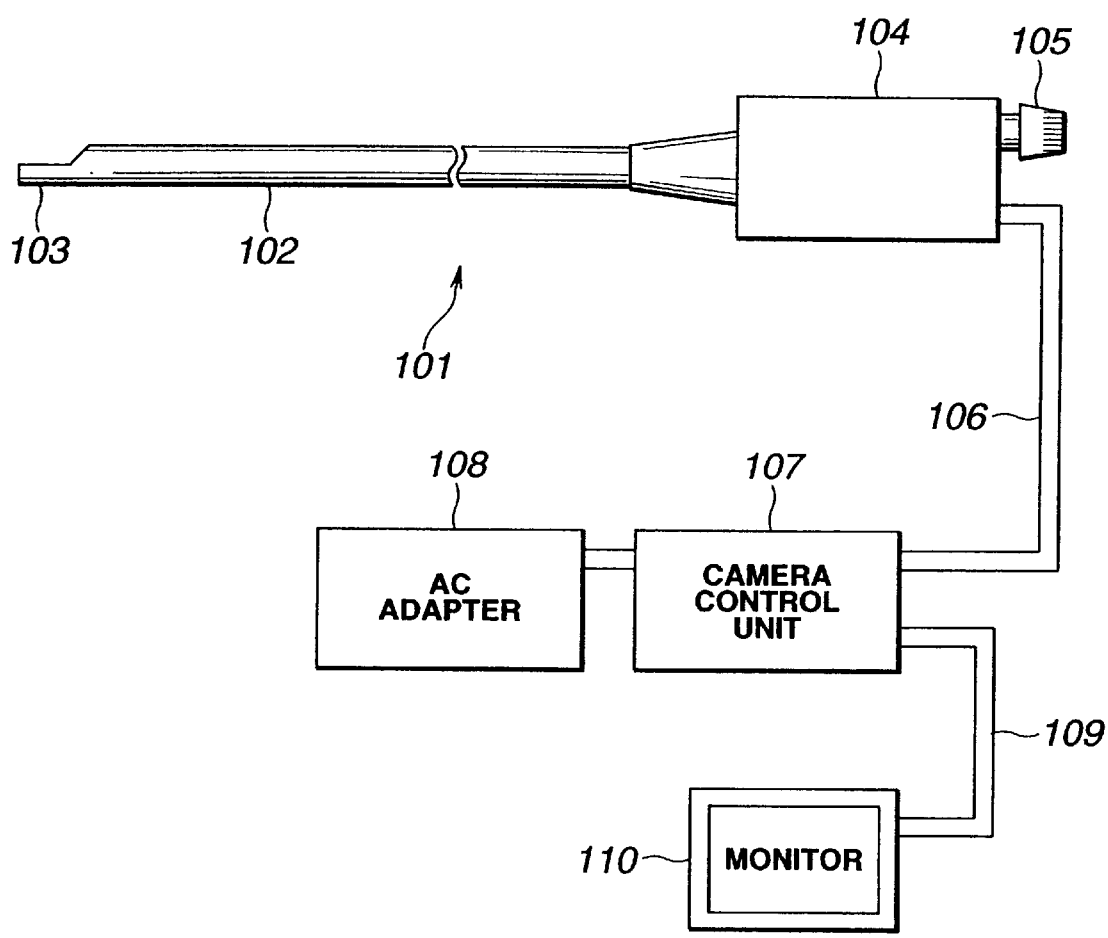
FIG. 11 to FIG. 21 relate to the second embodiment of the present invention.

As shown in FIG. 11, a side viewing endoscope 101 has an insertion unit 102 that is inserted into an intracorporeal cavity. A distal endoscope part 103 (hereinafter referred to as a distal part) in accordance with the present embodiment attached to the distal end of the insertion unit 102 has an imaging means and light emitting diodes serving as an illuminating means. A control unit 104 attached to the proximal end of the insertion unit 102 has a light level adjustment knob 105 used to adjust an amount of light emitted from the light emitting diodes in the distal part 103.

An optical image of an object illuminated by the light emitting diodes is projected on an imaging unit in the distal part 103, and converted into an electric signal. The electric signal is sent to a camera control unit 107 over a camera control cable 106. Image data represented by the electric signal is processed by the camera control unit 107 that is powered by an AC adapter 108. An image signal produced by the camera control unit 107 is transferred to a monitor 110 over a monitor cable 109. Consequently, an endoscopic image is displayed.

Figure 12:
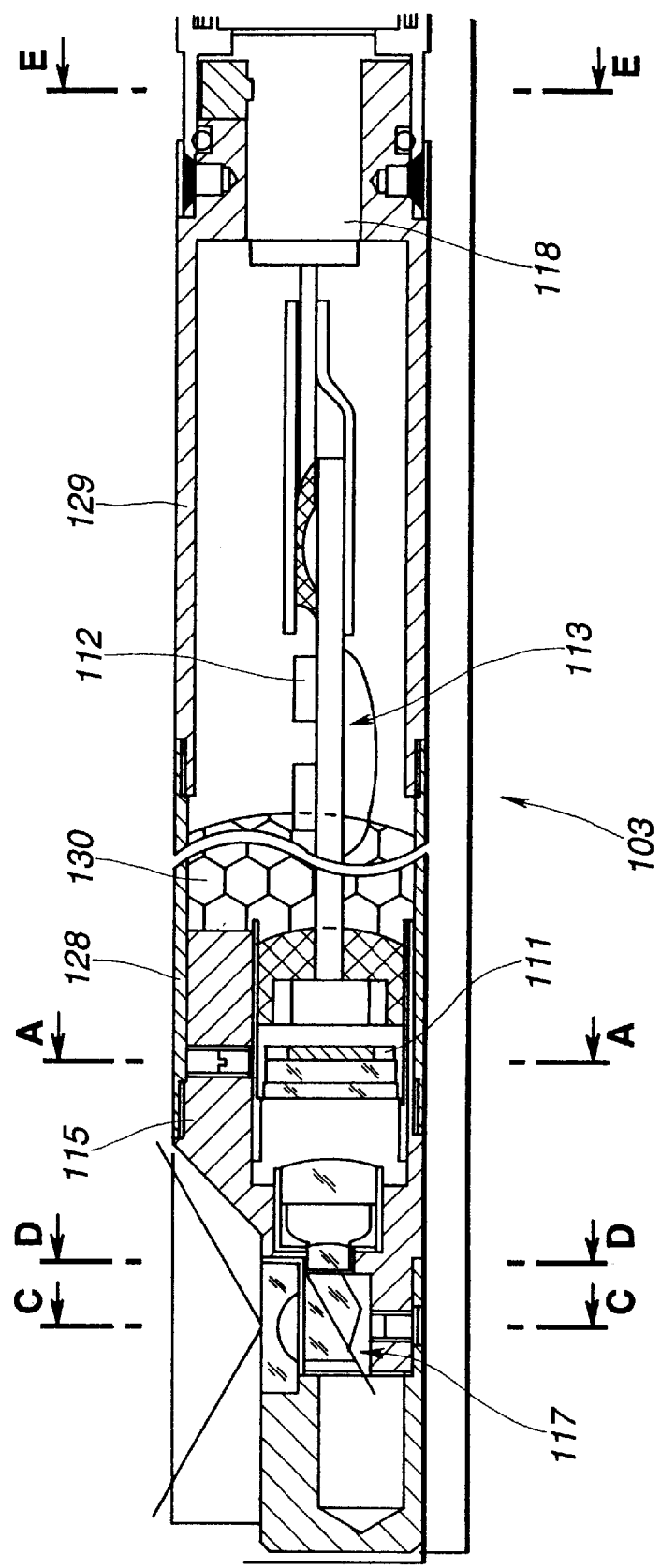
Figure 13:
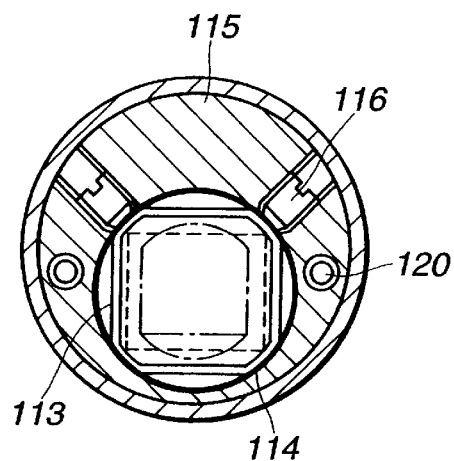

As shown in FIG. 12 and FIG. 13, an imaging unit 113 for converting an optical signal to an electric signal is fixed to a body 115 in the distal part 103 with a holder 114 between them by means of screws C 116. The imaging unit 113 consists of a solid-state imaging device 111 and electronic parts 112.

Moreover, an objective sub-assembly 117 for converging an optical image at the solid-state imaging device 111 is located ahead of the solid-state imaging device 111. The optical image represents an object located in a direction of side viewing (at a right angle with respect to the longitudinal direction of the insertion unit 2).

A signal cable 118 over which a signal is transferred from the camera control unit 107 to the imaging unit 113, and power cables 120 over which power is supplied to the light emitting diodes 119 are passed through the insertion unit 102. The light emitting diodes 119 serve as an illuminating means and will be described later.

Figure 14:
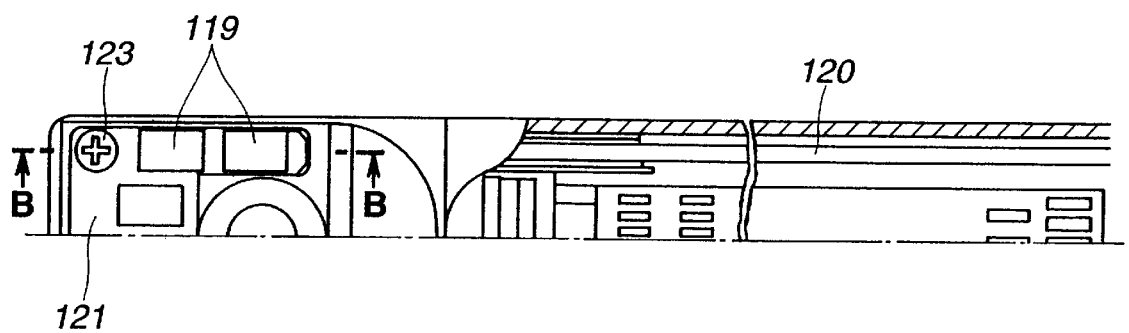
Figure 15:
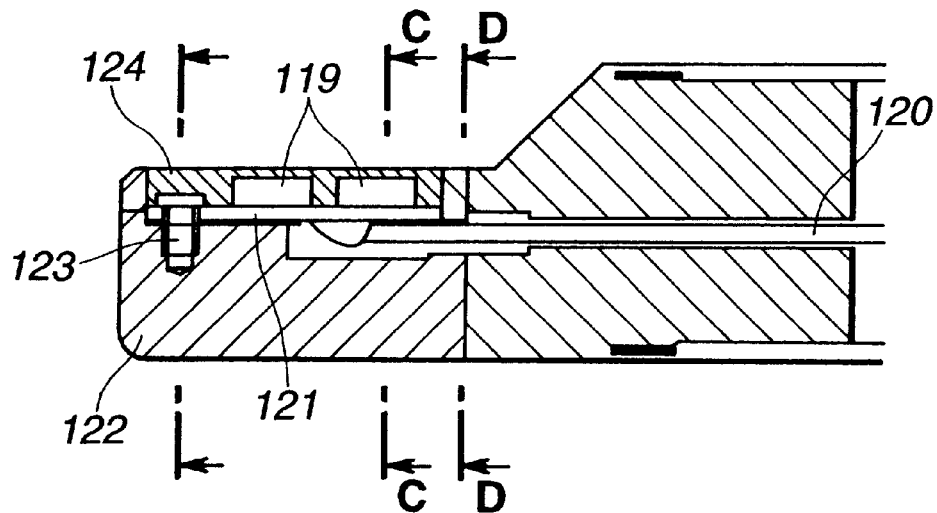

As shown in FIG. 14 and FIG. 15, the light emitting diodes 119 serving as an illuminating means for irradiating illumination light in the direction of side viewing (at a right angle with respect to the longitudinal direction of the insertion unit 102) are soldered to a substrate 121. The power cables 120 are also soldered to the substrate 121. The substrate 121 having the light emitting diodes and power cables united therewith is fixed to a body 122 by means of screws A 123.

The light emitting diodes 119 are fixed to the body 122 together with the substrate 121. Thereafter, a substantially transparent filler 124 is injected to fully cover the surroundings of the light emitting diodes 119 including the light emitting surfaces thereof. Even the tops of the light emitting diodes 119 are covered with the filler 124, whereby the light emitting diodes 119 are not only protected to be blocked from outside but also left watertight.

Figure 16:
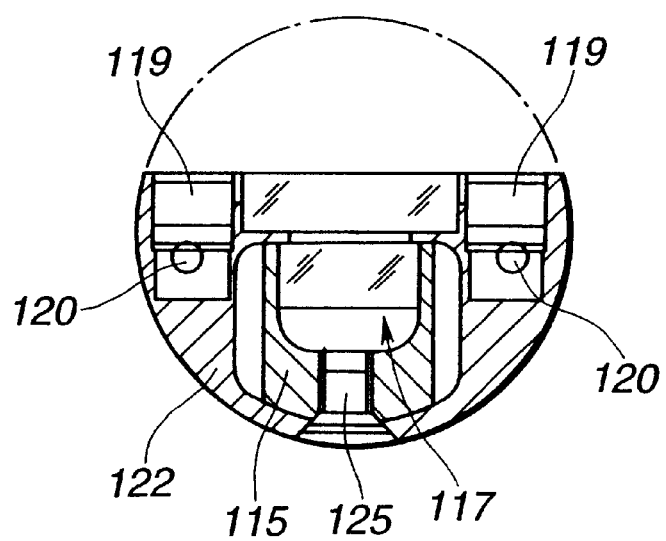
Figure 17:
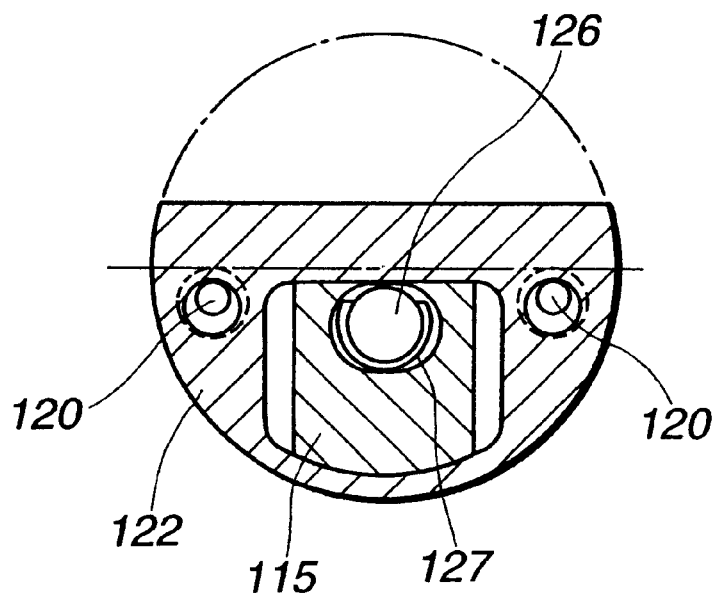

As shown in FIG. 16 and FIG. 17, the body 115 and body 122 are secured by a screw B 125. Part of a lens frame 127 mounted on the outer circumference of an objective 126 located behind a prism and included in the objective sub-assembly 117 is notched. This is because the dimension between the objective 126 and the body 115 that is a mate member is not large enough to tolerate the thickness of the lens frame 127.

Referring back to FIG. 12, a cover A 128 screwed to the body 115 is fixed to the outer circumference of the imaging unit 113. A cover B 129 is screwed to the cover A 128. The outer circumference of the imaging unit 113 is thus covered by two covers of the cover A 128 and cover B 129. This is intended to reinforce the fixation of the imaging unit 113 to the body 115 after the imaging unit is screwed firmly to the body 115. An adhesive 130 is therefore injected into a space created by the cover A 128, body 115, and imaging unit 113. Since two covers are used in combination, a desired position can be looked at accurately during work. The adhesive 130 can be injected easily.

Figure 18:
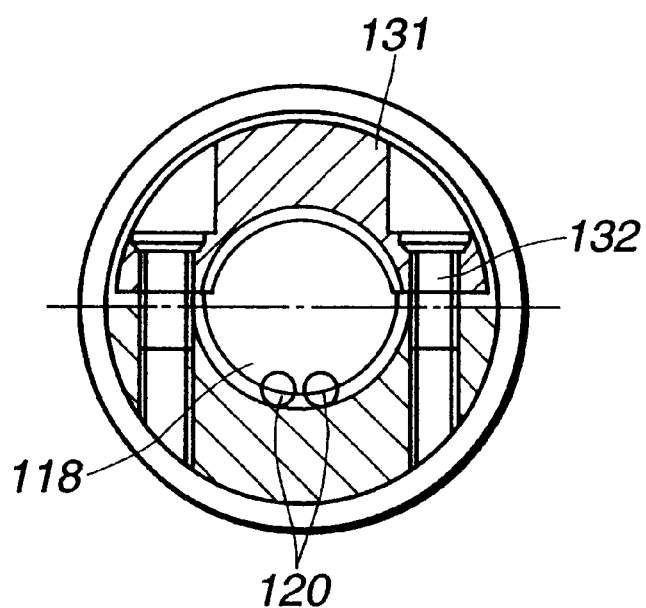

Moreover, as shown in FIG. 18, the signal cable 118 and power cables 120 are sandwiched between the cover B 129 and a fixture 131. The tensile strengths in the axial direction of the cables are thus improved. The fixture 131 is fixed to the cover B 129 by screws D 132.

Figure 19:
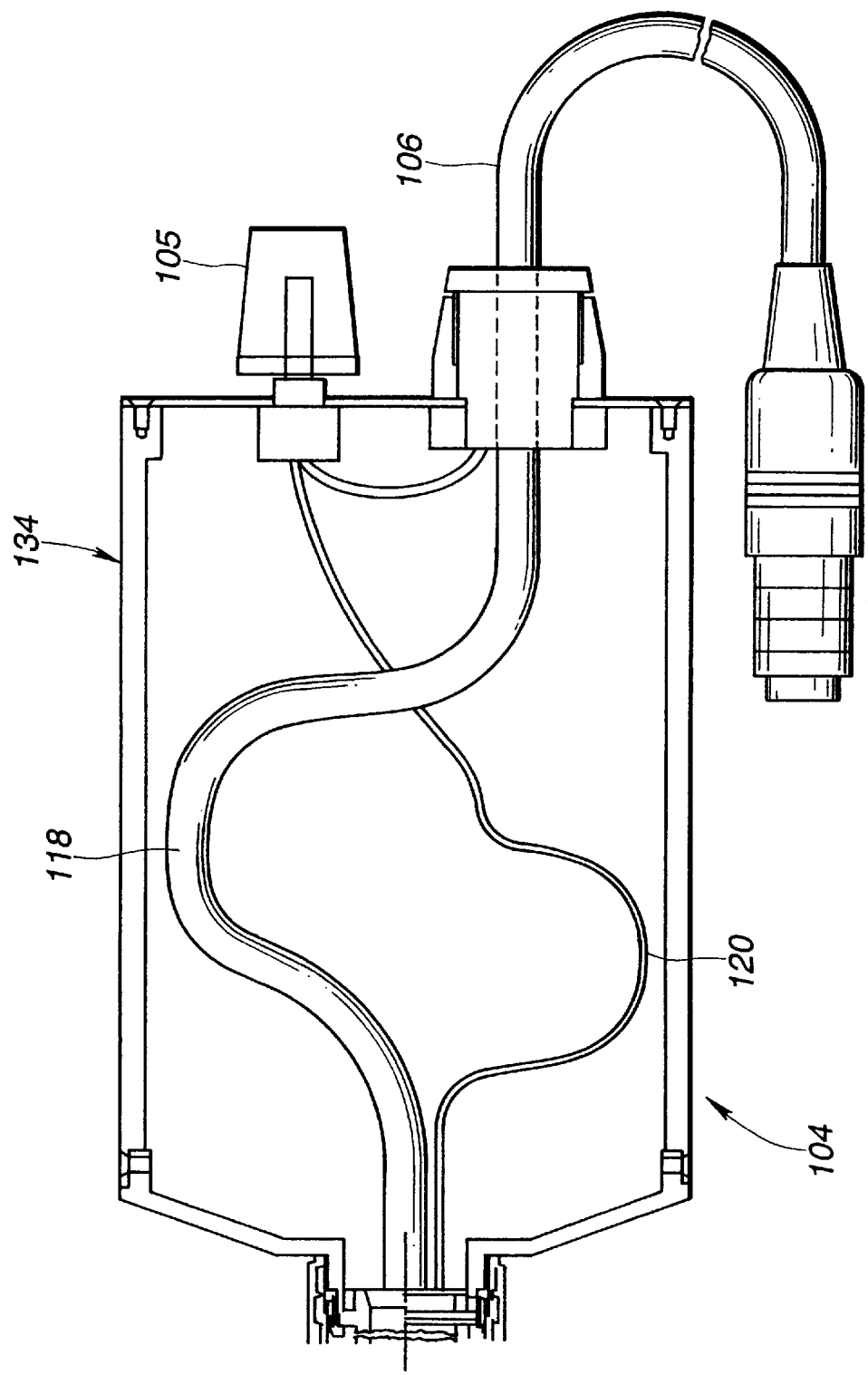

FIG. 19 shows the system control unit 103 shown in FIG. 11. The light level adjustment knob 105 is located on a back end panel 133 of the control unit 104. The light level adjustment knob 105 is structured not to jut out beyond the outer circumference 134 of the control unit 104. Even if a worker nonchalantly places the endoscope at a site, the switches including the light level adjustment knob 105 will hardly be flawed.

Figure 20:
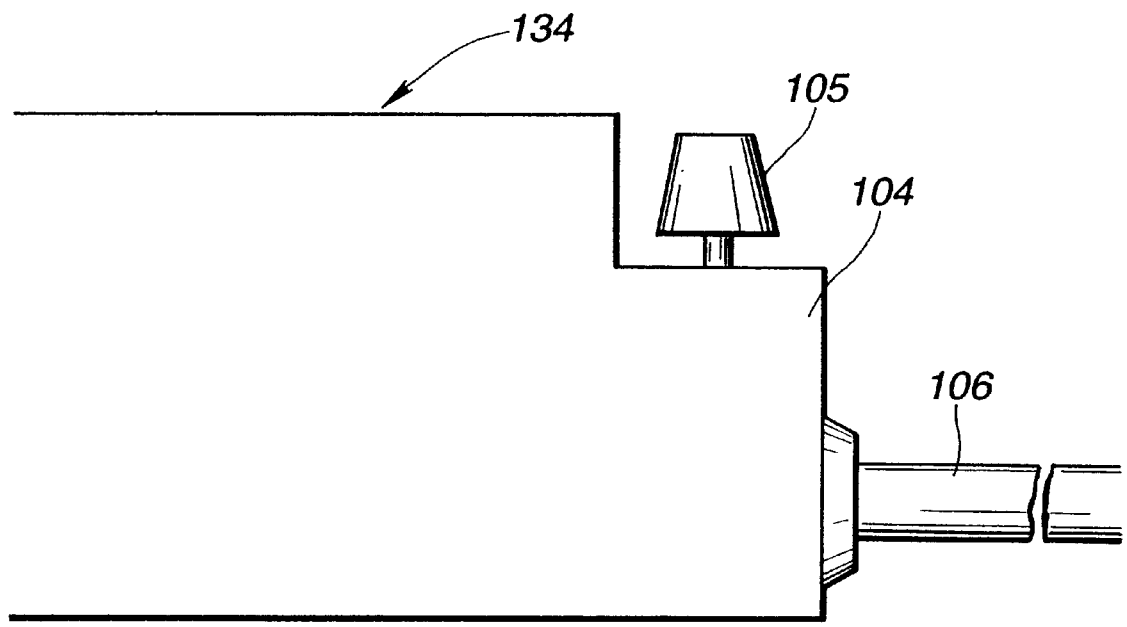

Moreover, the light level adjustment knob 105 may be, as shown in FIG. 20, located on the circumference of the control unit 104. In this case, the light level adjustment knob 105 will not jut out beyond the outer circumference 134.

Figure 21:
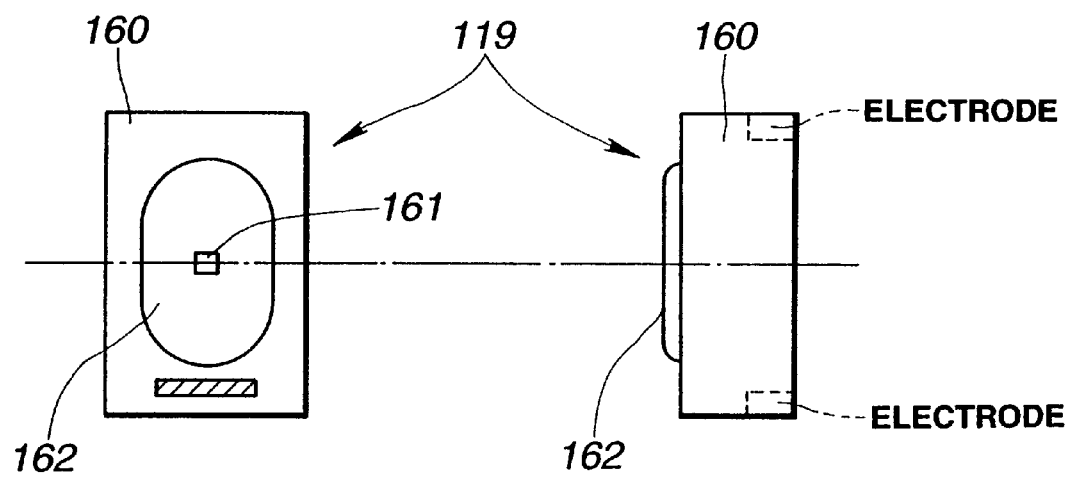

FIG. 21 shows the outline of a light emitting diode 119 employed in the second embodiment. The light emitting diode 119 is made by putting a chip (light emitting device) 161 in a center dent of a ceramic package 160 and covering the chip portion with a silicon resin 162.

As mentioned above, in this embodiment, the light emitting diodes 119 are fixed to the body 122 together with the substrate 121. Thereafter, the substantially transparent filler 124 is injected to fully cover the surroundings of the light emitting diodes 119 including the light emitting surfaces thereof. Since the tops of the light emitting diodes 119 are covered with the filler 124, it is unnecessary to place a transparent member in front of the light emitting diodes 119 and to increase the outer diameter of the distal part. Moreover, the light emitting diodes 119 can be not only protected to be blocked from outside but also left watertight.

The surroundings of the light emitting diodes and the front light emitting surfaces thereof are covered with the filler in order to realize a watertight structure. This makes it unnecessary to ensure a thickness large enough to support a transparent member used to attain a watertight state in the related art. The outer diameter of the distal part can therefore be made smaller. Moreover, the employment of the filler requires a smaller number of members than the employment of the transparent member such as a glass. Besides, the price of the distal part can be lowered.

Third Embodiment

The third embodiment is substantially identical to the second embodiment. Only a difference will be described. The same reference numerals will be assigned to identical components.

Figure 22:
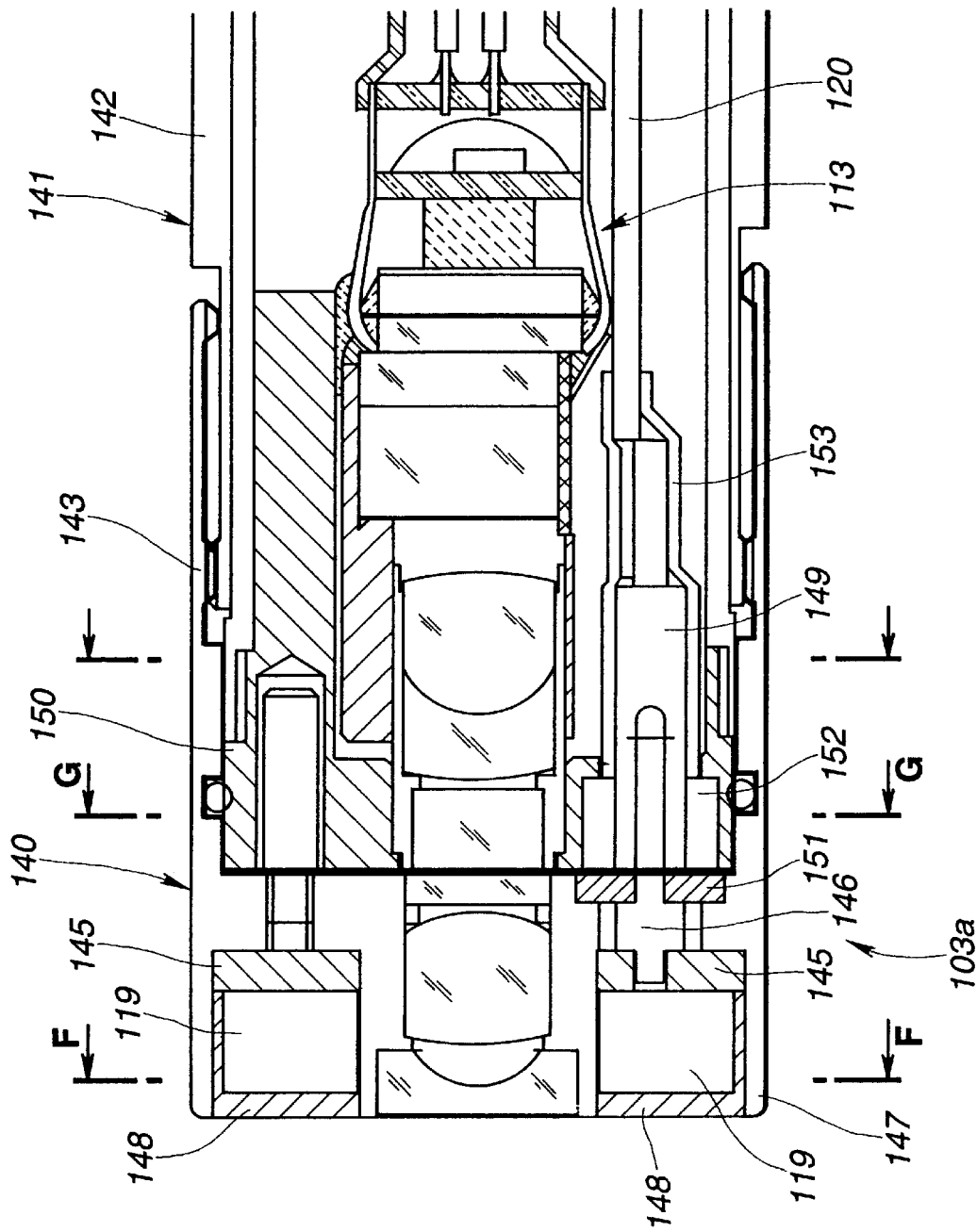
FIG. 22 to FIG. 24 relate to the third embodiment of the present invention.
Figure 23:
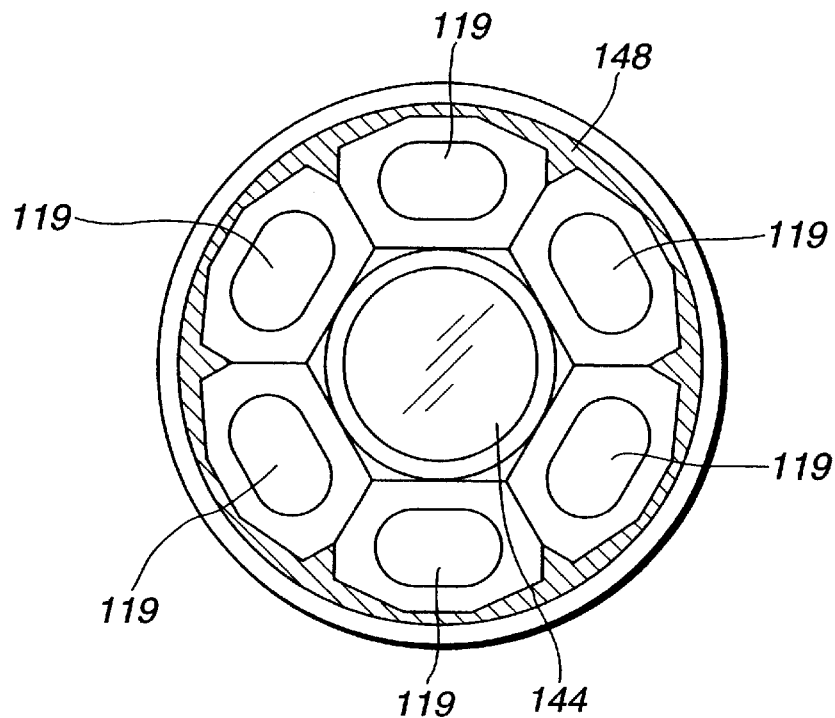
Figure 24:
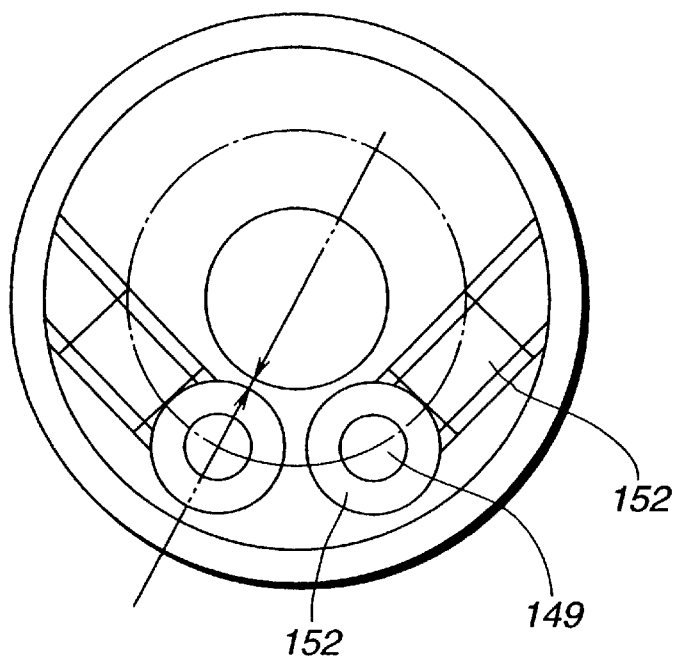

As shown in FIG. 22 to FIG. 24, a distal endoscope part 103*a* in accordance with the present embodiment is a distal part for a direct viewing endoscope. An insertion unit including the distal endoscope part 101*a* consists of an optical adapter 140 and an endoscope body 141. The optical adapter 140 is mounted on the outer circumference of the endoscope body 141 and secured to a setscrew 142, which can rotate only in a circumferential direction, by means of attaching screws 143.

A plurality of light emitting diodes 119 is placed on the circumference of an objective 144 in the optical adapter 140 with the objective 144 as a center (see FIG. 23). The light emitting diodes 119 are mounted on substrates 145 together with contact pins 146. The substrates 145 are stowed in an adapter body 147 with the light emitting diodes and contact pins united therewith. Thereafter, a substantially transparent filler 148 is injected to fully cover the light emitting diodes 119 including even the tops thereof. The light emitting diodes 119 are thus left watertight.

Power is supplied from the endoscope body 141 to the light emitting diodes 119 in the optical adapter 140 over power cables 120. Specifically, power is delivered to the contact pins 146 in the optical adapter 140 through contact receptacles 149 over the power cables 120. The power is then supplied to the light emitting diodes 119 via the substrates 145. A power supply member shall be composed of the contact receptacles 149 and contact pins 146. The power supply member is isolated from the metallic member of the body 150 by insulators A 151, insulators B 152, and insulating tubes 153, and secured by screws 154 (see FIG. 24).

Even in this embodiment, the filler 148 is injected to fully cover the light emitting diodes 119 including the tops thereof. The light emitting diodes 119 are thus left watertight. The same advantage as that provided by the second embodiment can therefore be provided.

In the present invention, it is apparent that a wide range of different embodiments can be constructed based on the invention without a departure from the spirit and scope of the invention. This invention will be limited by the appended claims but not restricted by any specific embodiments.

What is claimed is:

1. A distal endoscope part having an imaging means on which an optical image is projected via an objective optical system and light emitting diodes for supplying illumination light which are placed as an illuminating means on the outer circumference of said objective optical system, wherein the surroundings of said light emitting diodes are filled with a filler.

2. A distal endoscope part according to claim 1, wherein said light emitting diodes irradiate said illumination light in a direction perpendicular to the longitudinal axis of an insertion unit, and said optical image falls on said objective optical system in the direction perpendicular to the longitudinal axis of said insertion unit owing to said illumination light irradiated from said light emitting diodes.

3. A distal endoscope part according to claim 1, wherein said light emitting diodes irradiate said illumination light in a direction of the longitudinal axis of said insertion unit, and said optical image falls on said objective optical system in the direction of the longitudinal axis of said insertion unit owing to said illumination light irradiated from said light emitting diodes.

4. An endoscope having an insertion unit that is inserted into a lumen, wherein the distal part of said insertion unit includes an objective optical system on which an optical image falls, light emitting diodes for supplying illumination light which are placed as an illuminating means on the outer circumference of said objective optical system, and an imaging means on which said optical image is projected via said objective optical system, and wherein the surroundings of said light emitting diodes are filled with a filler.

5. An endoscope according to claim 4, wherein a light level adjusting means used to adjust an amount of light emitted from said light emitting diodes is located at the proximal end of said insertion unit.

6. An endoscope according to claim 4, wherein said light emitting diodes irradiate said illumination light in a direction perpendicular to the longitudinal axis of said insertion unit, and said optical image falls on said objective optical system in the direction perpendicular to the longitudinal axis of said insertion unit owing to said illumination light irradiated from said light emitting diodes.

7. An endoscope according to claim 6, wherein a light level adjusting means used to adjust an amount of light emitted from said light emitting diodes is located at the proximal end of said insertion unit.

8. An endoscope according to claim 4, wherein said light emitting diodes irradiate said illumination light in a direction of the longitudinal axis of said insertion unit, and said optical image falls on said objective optical system in the direction of the longitudinal axis of said insertion unit owing to said illumination light irradiated from said light emitting diodes.

9. An endoscope according to 8, wherein a light level adjusting means used to adjust an amount of light emitted from said light emitting diodes is located at the proximal end of said insertion unit.

* * * * *